United States Patent [19]
Aussel

[11] Patent Number: 5,035,144
[45] Date of Patent: Jul. 30, 1991

[54] FREQUENCY BROADBAND MEASUREMENT OF THE CHARACTERISTICS OF ACOUSTIC WAVES

[75] Inventor: Jean-Daniel Aussel, Longueuil, Canada

[73] Assignee: National Research Council of Canada, Ottawa, Canada

[21] Appl. No.: 386,771

[22] Filed: Jul. 31, 1989

[51] Int. Cl.$^5$ ............................................. G01N 29/00
[52] U.S. Cl. ..................................................... 73/602
[58] Field of Search .................... 73/602, 597, 598, 599

[56] References Cited

U.S. PATENT DOCUMENTS

| | | | |
|---|---|---|---|
| 4,372,163 | 2/1983 | Tittmann et al. | 73/602 |
| 4,633,715 | 1/1987 | Monchalin | 73/657 |
| 4,659,224 | 4/1987 | Monchalin | 356/352 |
| 4,688,429 | 8/1987 | Holroyd | 73/602 |
| 4,899,589 | 2/1990 | Thompson et al. | 73/602 |

OTHER PUBLICATIONS

"Study of Surface Acoustic Wave Dispersion Using Laser-Ultra-sonics and Application to Thickness Measurement" by J-D Aussel and J-P Monchalin, Review of Progress in NDE vol. 8A, Aug. 1989.
Physical Acoustics, Editors, W. P. Mason and R. N. Thurston; Academic Press, N.Y., vol. 12, Chapter 5, (9176), pp. 277–374, "Ultrasonic velocity and attenuation measurement methods with scientific and industrial applications" by E. P. Papadakis.
Ultrasonics, Mar. 1985, pp. 55–62, "Laser generation of convergent acoustic waves for material inspection" by P. Cielo et al.
Applied Physics Letters, vol. 52, No. 14, 1987, pp. 1066–1068, "Estimation of the thickness of thin metal sheets using laser generated ultrasound" by R. J. Dewhurst et al.
Canadian Journal of Physics, vol. 64, No. 9, 1986, pp. 1247–1264, "Mechanisms of pulsed photoacoustic generation" by D. A. Hutchins.
Ieee Trans. on Ultrasonics, Ferroelectrics, Frequency Control, vol. UFFC-33, No. 5, 1986, pp. 485–489, "Optical Detection of Ultrasound", J-P. Monchalin.
J. of Appl. Phys., vol. 49, No. 8, 1978, pp. 4320–4327 "On the determination of phase and group velocities of dispersive waves in solids" Sachse et al.
"Review of Progress in Quantitative Non Destructive Evaluation" in San Diego, CA, on Aug. 4, 1988, J-D. Aussel et al., Abstract.

Primary Examiner—Hezron E. Williams
Assistant Examiner—Louis M. Arana
Attorney, Agent, or Firm—Swabey Ogilvy Renault

[57] ABSTRACT

Frequency broadband measurement of the characteristics of acoustic waves propagating in an object is disclosed. A time domain signal processing is described, based on narrow-band filtering of wide-band acoustic wave pulses and cross-corelation which permits to measure both phase and group velocities as a function of frequency.

17 Claims, 9 Drawing Sheets a) 3mm DIAMETER ANNULAR SOURCE b) 15mm DIAMETER ANNULAR SOURCE

FREQUENCY BROADBAND MEASUREMENT OF THE CHARACTERISTICS OF ACOUSTIC WAVES

FIELD OF THE INVENTION

The present invention relates to a frequency broadband measurement of the characteristics of acoustic waves. In particular, it is directed to a frequency broadband (wide-band) measurement in which a time domain signal processing technique is used together with narrow-band filtering of wide-band (broadband) acoustic wave pulses propagating in an object.

BACKGROUND OF THE INVENTION

Acoustic waves are dispersive, when their phase and group velocities are frequency dependent. This dispersion may be caused by elastic property gradient (e.g. in composite materials) or by guided propagation (e.g. propagation in plates, rods and fibers). The attenuation of acoustic wave can be caused by various phenomena, including scattering by the microstructure of the sample under test, thermoelastic or heating effects, magnetoelastic loss effects in ferromagnetic materials and others. The measurement of dispersion, i.e. the determination of the phase and group velocities versus frequency, and of the attenuation can provide useful information on the specimens under test and its material properties. Acoustic dispersion measurements have been used to characterize subsurface anomalies, to estimate physical property gradients, to evaluate the thickness, the elastic properties or the microstructure of thin films, and to characterize composite materials. Attenuation measurements have been used to characterize the microstructure and various physical properties. See Physical Acoustics, Editors, W. P. Mason and R. N. Thurston, Accademic Press., N.Y., Vol. 12, Chapter 5 (1976), pp 277–374, "Ultrasonic velocity and attenuation measurement methods with scientific and industrial applicarions" by E. P. Papadakis; Ultrasonics, Mar. 1985, pp 55–62, "Laser generation of convergent acoustic waves for material inspection" by P Cielo et al. and Applied Physics Letters, Vol. 52, No. 14, 1987, pp 1066–1068, "Estimation of the thickness of thin metal sheets using laser generated ultrasound", by R. J. Dewhurst et al.

In most cases, acoustic waves are generated and detected using piezoelectric transducers either in direct contact with the sample or coupled to it with a liquid couplant. However in the cases where samples are at elevated temperatures or in motion etc., laser-ultrasonics is often employed which uses lasers to generate and detect ultrasound, without contact and at distance. See Canadian Journal of Physics, Vol. 64, NO. 9, 1986, pp 1247–1264, "Mechanisms of pulsed photoacoustic generation" by D. A. Hutchins and IEEE Transactions on Ultrasonics, Ferroelectrics, Frequency Control, Vol. UFFC-33, No. 5, 1986, pp 485–489, "Optical detection of ultrasound" by J-P Monchalin.

Historically, measurement techniques for the determination of the attenuation and of the phase and group velocities have evolved from discrete-frequency methods, such as the $\pi$-point phase technique or the toneburst method, to a frequency-wideband method based on spectral analysis. The $\pi$-point phase technique and the tone-burst methods are harmonic methods, i.e. the acoustic waves are generated and detected at a single frequency, and the attenuation and the phase and group velocities are measured at this single frequency. A drawback of these harmonic methods is the necessity of a harmonic acoustic source of easily variable frequency. The spectral analysis method has been reviewed in Journal of Applied Physics Vol. 49, No. 8, 1978, pp 4320–4327 "On the determination of phase and group velocities of dispersive waves in solids" by Sachse et al. U.S. Pat. No. 4,372,163 Feb. 8, 1983 (Ahlberg et al) also describes this technique. The spectral analysis method using Fourier transform has the advantage of providing a broad frequency coverage from the analysis of the spectrum of short pulsed acoustic waves. When several propagating acoustic modes are mixed, as it is the case in waveguides (plates, rods, fibers) for example, the spectral analysis method is not applicable because the spectrum of the measured acoustic wave is an average of the spectra of the mixed waves. The information on each mode is thus mixed both in frequency and time. As a result, there is at least one case where these classical methods cannot be used: when a monochromatic acoustic source is difficult to realize, the harmonic methods are not usable, and when several propagating acoustic modes are mixed, the spectral analysis method is not applicable. The present invention is a solution for such cases and processes broadband acoustic waves. The mixed modes may be identified after narrow-band filtering and separated before processing.

SUMMARY OF THE INVENTION

The present invention is directed to a method of and apparatus for measuring the characteristics of acoustic waves propagating in an object for the purpose of nondestructive evaluation of the object. Briefly stated, the method includes steps of generating in the object frequency broadband acoustic waves and detecting the acoustic waves at a first and a second locations along the object for producing a first and a second broadband signals respectively. The method further includes steps of filtering the first and second broadband signals at a center frequency F, to produce a first and a second narrow-band signals respectively and obtaining the phase propagation time TP at the frequency F of the acoustic waves propagating in the object by processing in the time-domain the first and the second narrow-band signals. According to further embodiments of the present invention, additional steps of obtaining the group propagation time TG and the attenuation ATT by processing the narrow-band signals can be included. The apparatus, on the other hand, comprises acoustic wave generating means, acoustic wave detecting means, filtering means and signal processing means.

The present invention was orally presented by the present inventor at "Review of Progress in Quantitative Non Destructive Evaluation", in San Diego, Calif. on Aug. 4, 1988. A written abstract accompanied the oral presentation but a detailed description was published in August 1989 in the Proceedings of the Review of Progress in Quantitative Non Destructive Evaluation, Vol. 8A, D. O. Thompson and D. E. Chimenti, Editors, pp 535–542.

OBJECTS OF THE INVENTION

It is therefore an object of the present invention to provide a method of and an apparatus for measuring the characteristics of acoustic waves propagating in an object.

It is another object of the present invention to provide a method of and an apparatus for measuring the characteristics of frequency broadband acoustic waves propagating in an object.

It is still another object of the present invention to provide a method of and an apparatus for measuring the characteristics of frequency broadband acoustic waves propagating in an object in which narrow-band filtering at a center frequency is used.

It is a further object of the present invention to provide a method of and an apparatus for measuring the characteristics of frequency broadband acoustic waves propagating in an object in which narrow-band filtering at a center frequency is used and phase velocity, group velocity, and attenuation are calculated thereafter.

BRIEF DESCRIPTION OF THE DRAWINGS

For more complete understanding of the present invention and for further objects and advantages thereof, references may be made to the following description taken in conjunction with the accompanying drawings in which.

DETAILED DESCRIPTION OF THE PREFERRED EMBODIMENTS

Figure 1:
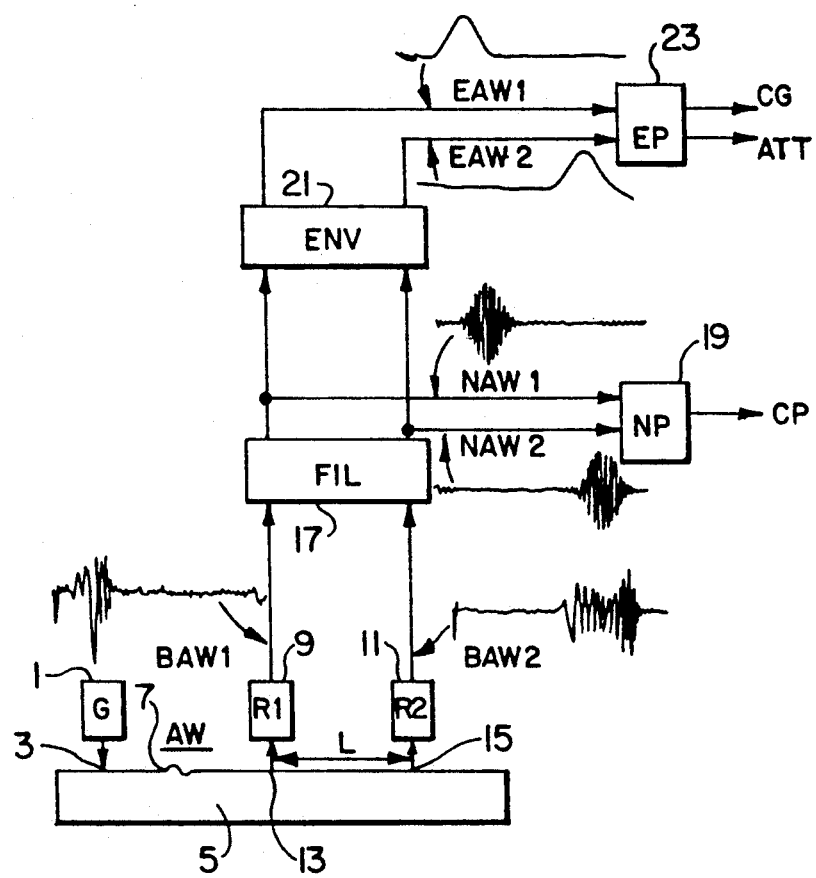
FIG. 1 is a brief diagrammatic illustration of the present invention according to one embodiment.

FIG. 1 is a brief diagrammatic illustration of the invention according to one embodiment. Frequency broadband acoustic waves are generated in pulses by a generator 1 at a location 3 at the surface of an object 5. The acoustic waves propagate in the object as well as along the surface thereof, depending upon the kind of material and structure of the object and the mode, frequency, etc. of the acoustic waves. The propagating acoustic waves shown schematically at 7 are detected by two frequency broadband receivers 9 and 11 at first and second locations 13 and 15 respectively, separated by a distance L, to produce first and second broadband signals. The first and second broadband signals which are shown schematically as BAW 1 and BAW 2 in the figure are filtered by a filter 17 at a center frequency F, hence giving first and second narrow-band signals respectively shown as NAW 1 and NAW 2. The filtering can be performed either with analog electronic filter of variable center frequency, or with a bank of analog filters of different fixed center frequencies, or with a digital electronic filter of programmable center frequency or with a bank of digital filters of different fixed frequencies or still by software with a computer or a microprocessor. The first and second narrow-band signals are sent to a narrow-band signal processor 19 to measure the time delay TP therebetween which is the phase propagation time of the acoustic waves at frequency F. The narrow-band signal processor 19 measures the time delay either by superimpostion or cross-correlation of the two narrow-band signals. The first and second narrow-band signals are also sent to an envelope generator 21 which generates first and second envelope signals of the first and second narrow-band signals respectively, indicative of energies thereof. The first and second envelope signals are shown schematically as EAW 1 and EAW 2 in the figure. The envelope signals can be obtained from analytic signal of the narrow-band signal or by a low-pass filter or the Hilbert transform.

The first and second envelope signals are sent to an envelope signal processor 23 to measure the time delay TG therebetween which is the group propagation time of the acoustic waves at frequency F. As in the measurement of time delay of two narrow-band signals, the two envelope signals can be superimposed or cross-correlated to measure the time delay. The attenuation ATT of the acoustic waves is calculated from the amplitudes of the envelope signals by an equation:

$$ATT = (\log R)/L$$

where R is equal to (Amplitude of the second envelope signal/Amplitude of the first envelope signal) and L is the distance between the first and second locations. The envelope signal processor 23 includes therein amplitude means for generating the amplitudes of the envelope signals and an amplitude processor for calculation according to the above equation.

The filtering and time delay measuring process can be repeated for a set of center frequencies F to obtain a set of attenuations ATT, a set of phase propagation times TP and a set of group propagation time TG. The set of phase propagation times is further processed to detect discontinuities which may cause by frequency dispersion and to generate a corrected set of phase propagation time TP'. The signal processor 19 uses an equation, $CP = L/TP'$ to generate the phase velocity CP of the acoustic waves for each varied frequency. The envelope signal processor 23 uses an equation, $CG = L/TG$, to produce the group velocity CG of the acoustic waves for each varied frequency.

Figure 2:
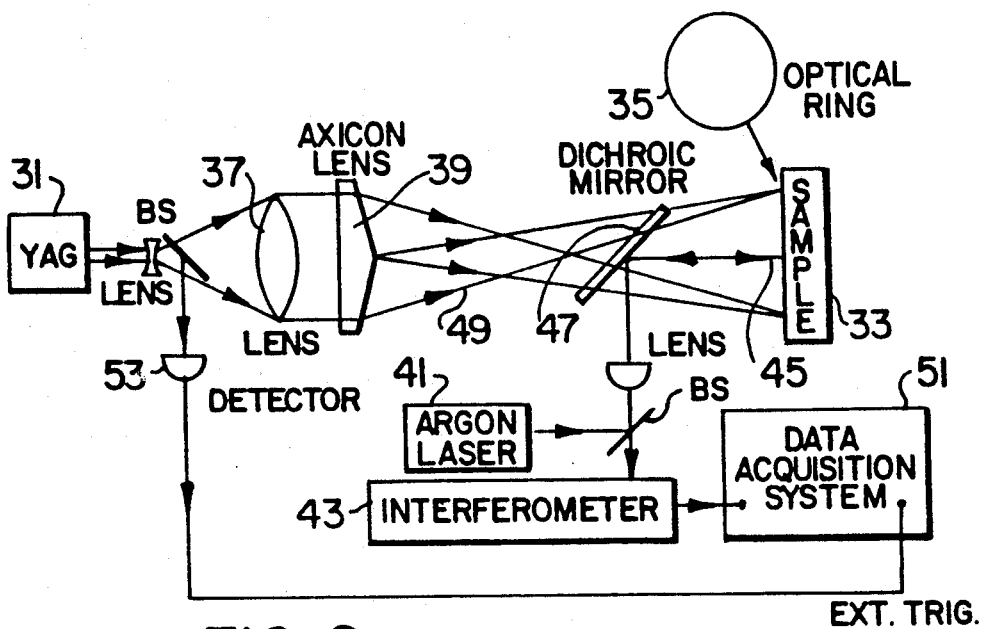
FIG. 2 is a schematic illustration of an actual experimental setup.
Figures 3A, 3B:
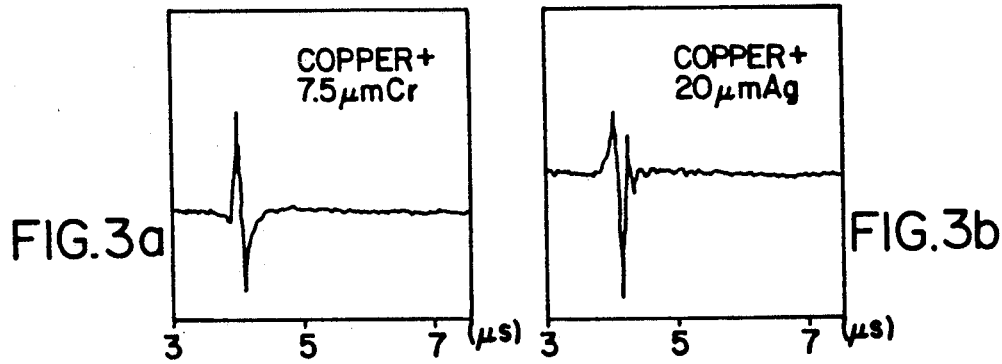
FIGS. 3a to 3f are graphs showing laser-detected signals of surface acoustic waves generated by a laser on a thick cooper substrate with coatings.
Figures 3C, 3D:
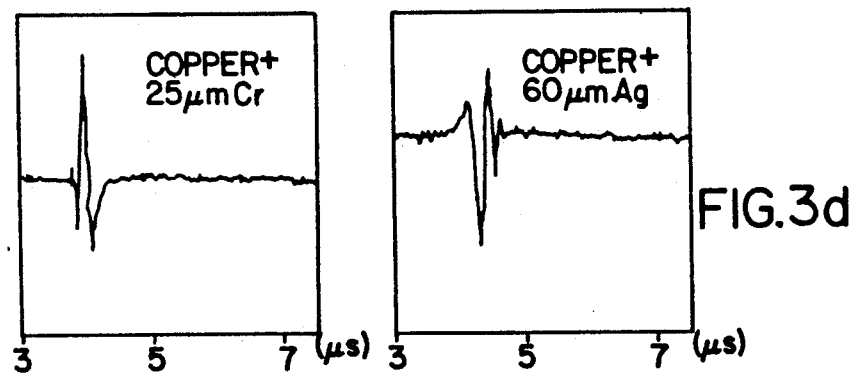
Figures 3E, 3F:
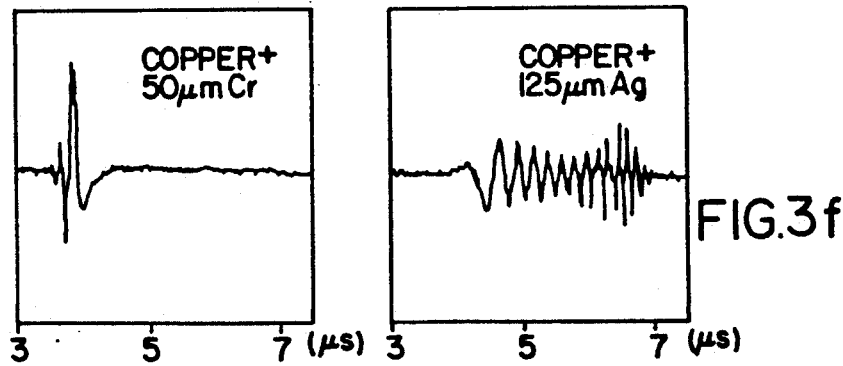

FIG. 2 shows schematically an experimental setup by which various experimental data were obtained as will be described later. A Nd:YAG laser 31 of 10 ns pulse duration, 0.75 J maximum energy is used for acoustic wave generation. A ring source is produced at the surface of a sample as illustrated at 35 by using a converging lens 37 and an axicon 39. The beam is sufficiently attenuated so that generation occurs in the thermoelastic regime. Most applications require conditions of generation which do not affect the surface of the specimen, i.e. operation in the thermoelastic regime. The ring source is used because in the operation in this regime, rather weak ultrasonic displacement signals are generally produced. However considerable enhancement of the signal has been demonstrated by distributing the laser energy on a circle and detecting the displacement at the center of convergence of the generated acoustic waves. See the above-referenced article in Ultrasonics by P Cielo et al. The ring diameter can be adjusted from 3 to 30 mm with a typical width of 0.2 mm by varying the axicon distance to the sample. The acoustic waves converging toward the center of the ring is detected by an argon laser 41 coupled to a heterodyne displacement interferometer 43. U.S. Pat. No. 4,633,715 Jan 6, 1987 (Monchalin) describes such an interferometer in detail. The probe beam 45 is focussed at the center of the ring through a dichroic mirror 47 which transmits the generating laser beam 49 but reflects light from the receiving argon laser 41. Data are gathered and processed by a data acquisition system 51. A detector 53 produces a signal which is used as triggering pulses for the data acquisition system.

In order to illustrate advantages of the present invention more clearly, the above-mentioned known spectral analysis method using the Fourier transform is discussed in detail in connection with the experimental setup shown in FIG. 2.

The Fourier transform of the converging acoustic waves generated by annulus of radius r can be expressed as $$u(r,f) = U_0(f) e^{-a(f,r)} e^{-i[2\pi fr/c - \phi_0(f)]} \quad (1)$$

where f is the frequency, $U_0(f)$ and $\phi_0(f)$ are the initial amplitude and phase terms due to thermoelastic generation, $a(f,r)$ is an attenuation propagation term, and $2\pi fr/c$ a phase propagation term. This term (the phase propagation term) can be determined by using two different ring sources of radii $r_1$ and $r_2$. From equation (1), the phase difference between the acoustic waves generated by sources of radii $r_1$ and $r_2$ is:

$$\delta_\phi = 2\pi f(r_1 - r_2)/c = 2\pi f t_p \quad (2)$$

Equation (2) shows that the phase velocity c, or the phase delay (or phase propagation time) $t_p$, can be determined from the phase difference of the two converging acoustic waves. This phase difference can be calculated either by Fourier transform of the two signals, or by Fourier transform of their cross-correlation using in addition a phase continuity algorithm to avoid $2\pi$ jumps. Concerning the precision of this spectral analysis method, which operates in the frequency domain (FD), the standard deviation error on the phase propagation time, $t_p$, is given by:

$$\sigma_{FD}(f) = [1 + 2SNR(f)]^{\frac{1}{2}} / 2\pi f \sqrt{2} \, SNR(f) \quad (3)$$

where SNR(f) is the frequency dependent signal-to-noise ratio. This error increases when the frequency or the signal-to-noise ratio decreases. An important limitation of this method originates from truncation of data. Truncation, or windowing, is needed to remove extra reflections or spurious signals, but it may strongly affect the phase spectra. The signal discontinuities at the edges introduce false frequency components, and the spectral leakage of the window integrates the noise over the entire frequency band. One should also note, that the frequency resolution of this frequency domain method is fixed by the discrete Fourier transform to 1/T, where T is the time duration of the truncated acoustic wave signal. From the phase velocity and its variation with frequency, the group velocity $c_g$ is then determined according to:

$$c_g = c^2 / (c - f \, dc/df) \quad (4)$$

This formula shows that the determination of the group velocity is very sensitive to errors on the phase velocity due to the derivative dc/df, so the group velocity determined in this way will be generally much less accurate than the phase velocity.

On the other hand, as described earlier, the present invention relates to a method of analysis which operates in the time domain (TD) and overcomes the above limitations.

This TD method is equivalent to the tone-burst method, except that in this case all the frequencies are obtained directly from the wideband acoustic waves and the narrow-band burst is obtained by digital processing instead of using a tuned pulsed oscillator. As in the case of the tone-burst method, an uncertainty of k/f, where k is an unknown integer and f is the center frequency of the burst, can appear in the measurement of the phase velocity in the case of highly dispersive media. As mentioned earlier, therefore, the phase propagation time TP must be corrected for this uncertainty. This uncertainty is eliminated in the corrected phase propagation time TP', by using a phase delay continuity algorithm to detect 1/f time jumps. This continuity algorithm is, as shown by equation (2), equivalent to the phase continuity algorithm used in the FD method.

The TD method has several advantages over the more classical FD method. Both phase and group velocities can be directly measured, the time truncation does not affect the crosscorrelation, mixed signals can sometimes be separated as will be shown below, and finally the time uncertainty could be made smaller with proper choice of the bandwidth of the narrow-band filters. The error on the phase delay measurement with the TD method is given by:

$$\sigma_{TD}(f) = \frac{[3(1 + 2\,SNR(f))]^{\frac{1}{2}}}{2\sqrt{2}\,\pi\sqrt{T}\,SNR(f)\,[(f + \Delta f/2)^3 - (f - \Delta f/2)^3]^{\frac{1}{2}}} \quad (5)$$

where T is the time duration of each narrow-band acoustic wave pulse, SNR(f) is the signal-to-noise ratio at the center frequency f, and $\Delta f$ is the bandwidth of the narrow-band filter. From equations (3) and (5), the ratio of the two standard deviation errors $\sigma_{FD}/\sigma_{TD}$ is given by:

$$\sigma_{FD}/\sigma_{TD} = [T\Delta f(1 + \Delta f^2/12 f^2)]^{\frac{1}{2}} \quad (6)$$

which reduces in practice to $(T\Delta f)^{\frac{1}{2}}$, since $\Delta f$ is generally less than f. This shows that the TD method is superior to the more traditional FD method when $f > 1/T$, i.e. when the bandwidth of the narrow-band filter is larger than the intrinsic frequency resolution of the discrete Fourier transform. It should be noted that this advantage does not appear very large if $\Delta f$ is kept sufficiently small for adequate resolution. However, the expression of $\sigma_{FD}$ does not take into account the additional spurious frequencies and additional noise introduced by truncation, which results in practice into a much larger gain in precision of the TD technique over the FD technique, as it is shown in the following experimental results.

a) Acoustic wave dispersion on a thick metallic layered substrate

The experimental setup of FIG. 2 was used to measure the surface wave dispersion on thick metallic samples. The samples used were 25 mm thick copper (Cu) substrates coated with silver (Ag) layers of 20, 60, and 125 μm thickness, or chromium (Cr) layers of 7.5, 25, and 50 μm thickness. The Rayleigh velocity of the copper being 2235 m/s, 25 mm corresponds to about 10 ultrasonic wavelengths at 1 MHz, so the substrate can be considered infinite for frequencies above 1 MHz. FIGS. 3a to 3f show laser-generated and detected converging surface acoustic wave (SAW) signals (arbitrary unit) on a thick copper substrate with silver or chromium coatings. The thermoelastic annular source is 15 mm in diameter. Dispersion effects, which increase with layer thickness, can be readily seen. In the case of the Cr layers, high frequency components have a higher velocity, whereas the opposite occurs with the Ag layers. This can be explained by the penetration of the SAW, which propagates in the solid to a depth of the order of its wavelength. Low frequencies penetrate deeper and tend to propagate in the substrate, whereas high frequencies have less penetration and propagate mainly in the layer. Cr having a faster shear and Rayleigh velocity than Cu, high frequencies consequently propagate faster, whereas the reverse occurs for Ag.

Figure 4A:
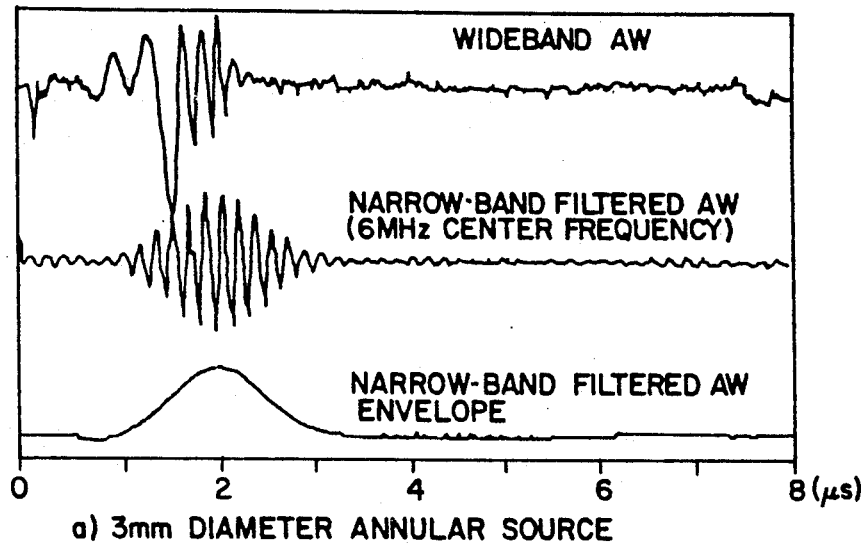
FIGS. 4a and 4b show various signals on a copper substrate with coatings generated by annular sources of different diameters.
Figure 4B:
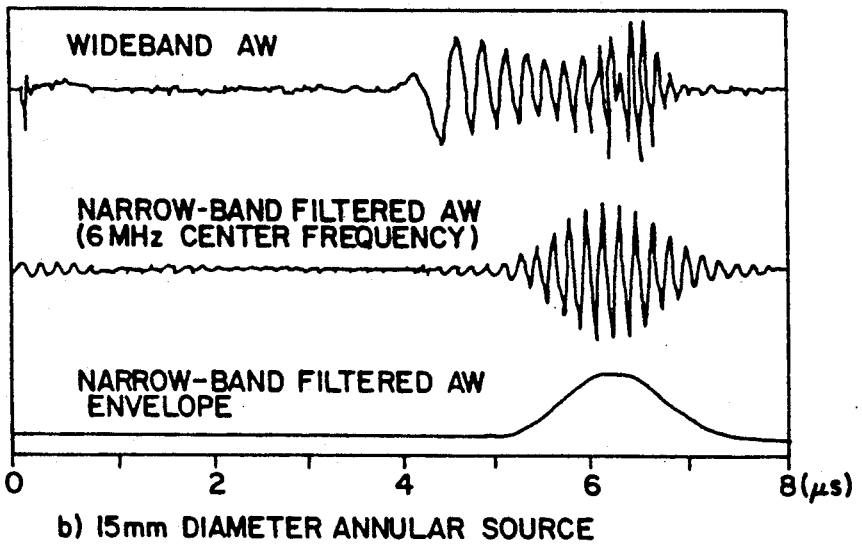
Figure 5A:
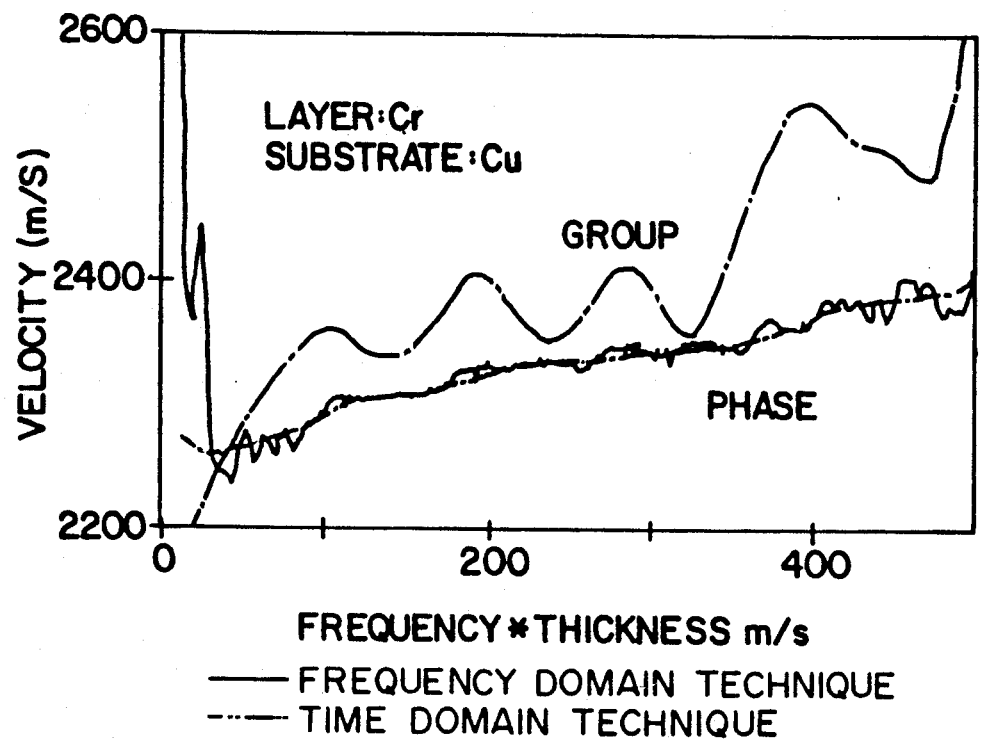
FIGS. 5a and 5b are graphs showing phase and group velocities measured by frequency domain and time domain methods.
Figure 5B:
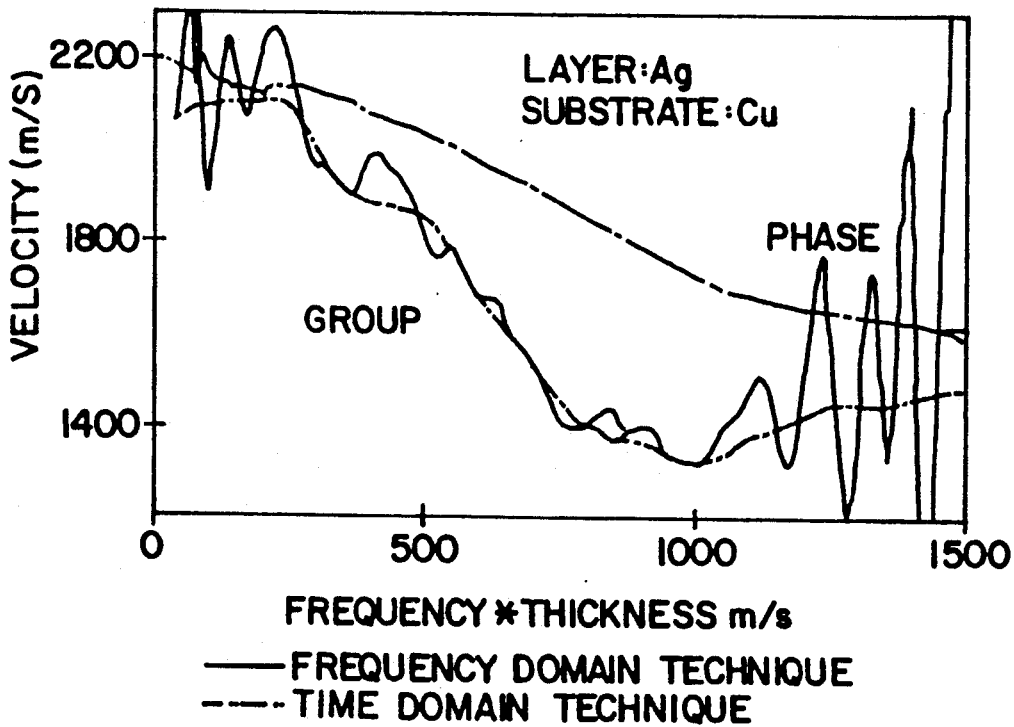

The time and frequency domain methods were applied to the above Cu substrates coated with Cr and Ag using ring sources of 3 mm and 15 mm diameter. FIGS. 4a and 4b show typical experimental signals and the corresponding signals obtained after filtering, as well as their envelope signals on a thick Cu substrate with a 125 μm layer of Ag. FIG. 4a includes broadband, narrowband and envelope signals in the case of the 3 mm diameter annular source and FIG. 4b shows corresponding signals for the 15 mm diameter annular source. The experimental phase and group velocities deduced from these signals by crosscorrelation (TD method) are shown by dotted lines in FIGS. 5a and 5b with the results obtained by the FD method by solid lines. It is clear that the TD method gives a better precision of determination of the phase velocity, particularly at low frequencies. In the case of the group velocity determination, the advantage of the TD method is even more obvious. With the FD method, meaningful group velocity results cannot be calculated in the case of the Cr layer, and large errors appear at high frequencies in the case of the Ag layer.

Figure 6A:
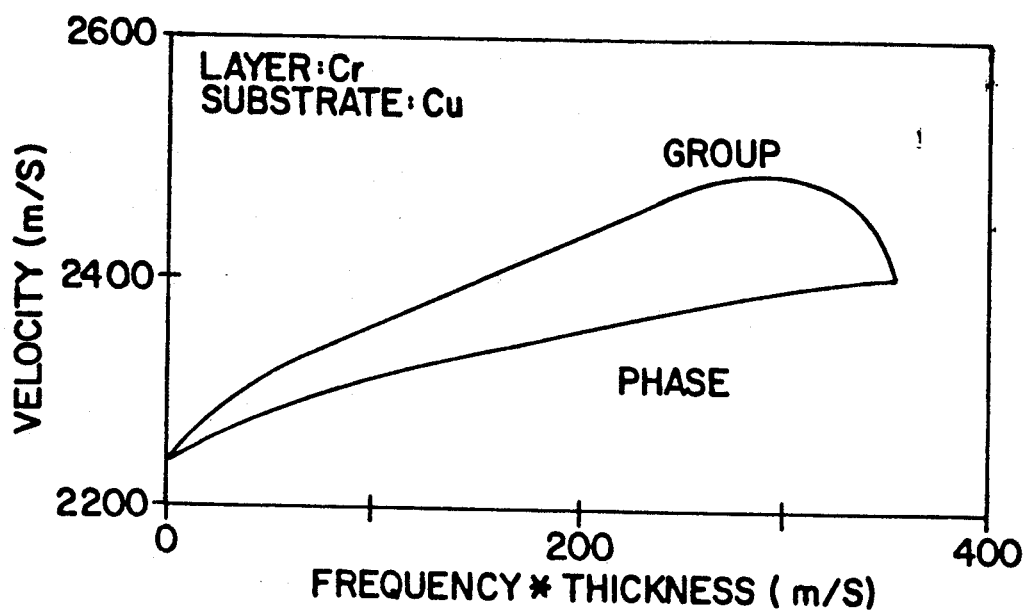
FIGS. 6a and 6b are graphs showing theoretical data for phase and group velocities.
Figure 6B:
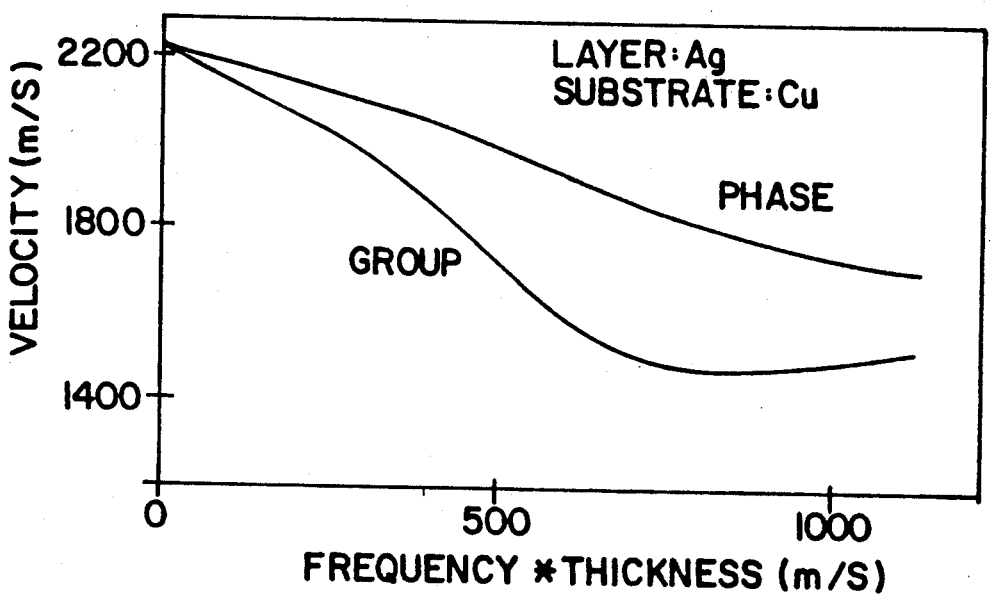
Figure 7C:
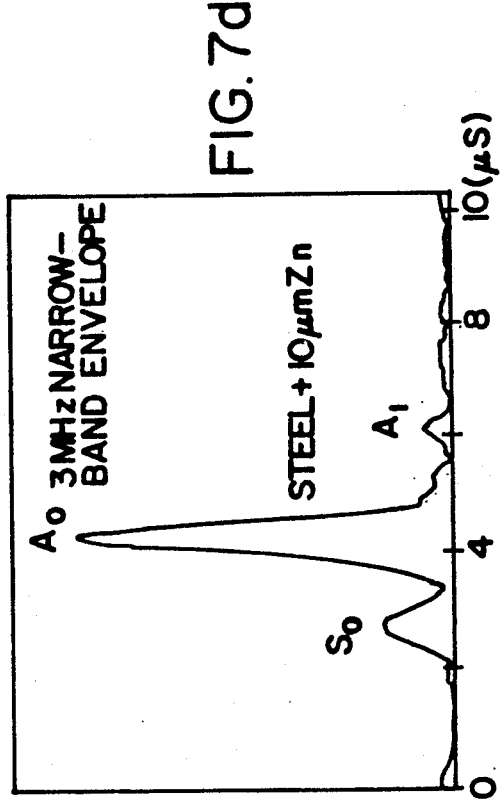
FIGS. 7a to 7d show results obtained in an experiment using an uncoated and coated steel specimens.
Figure 7D:
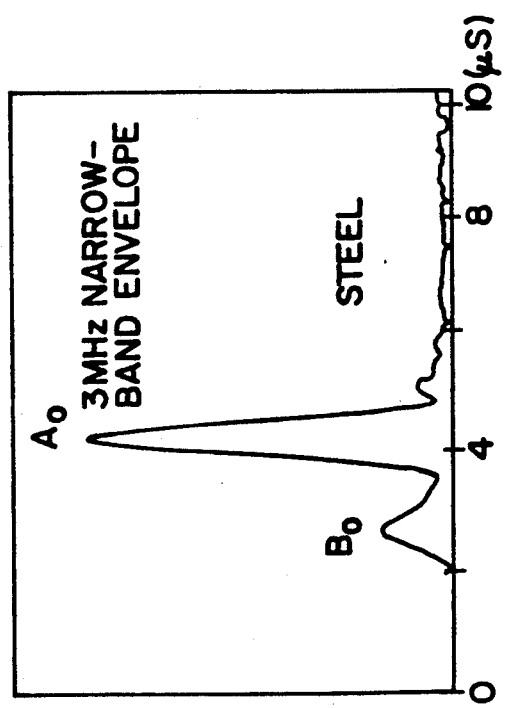
Figure 7A:
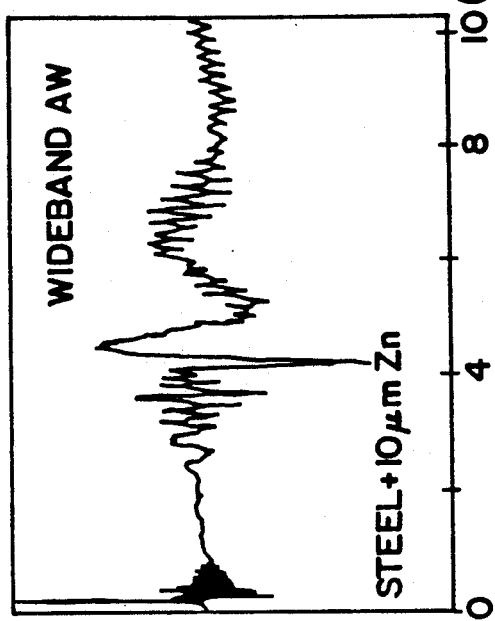
Figure 7B:
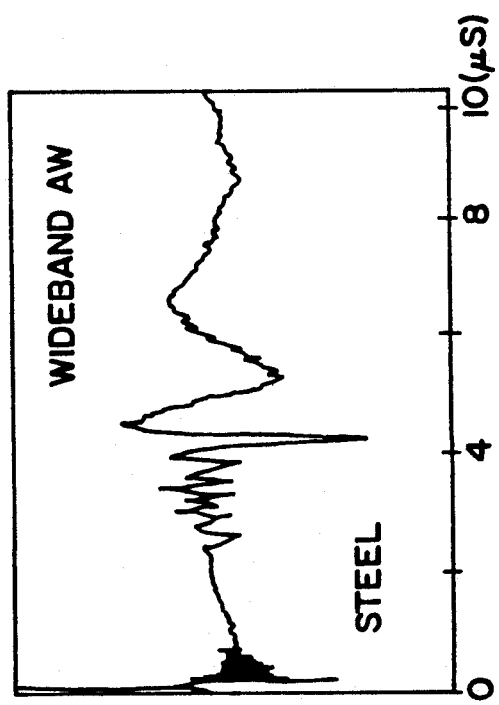

These experimental results were then compared to theoretical data obtained with a computer program which is based on the harmonic solution of the equation of motion with appropriate boundary conditions. FIGS. 6a and 6b show theoretical data for SAW phase and group velocities on a thick Cu substrate with an Ag or Cr layer. The velocities vary from the Rayleigh velocity in the substrate at low frequency*thickness values, to the Rayleigh velocity of the layer at high frequency*thickness values. Rayleigh velocities are Cu:2235 m/s, Cr:3655 m/s, Ag:1658 m/s and shear velocities are Cu:2395 m/s, Cr:4005 m/s and Ag:1770 m/s. In the case of the Cr coating, dispersion curves cannot be calculated with this program above the shear velocity of the copper substrate. By comparing FIGS. 5a, 5b and FIGS. 6a, 6b, a good qualitative agreement can be observed between the experimental and theoretical results.

b) Acoustic wave dispersion on a sysmmetrically layered thin substrate

The study of this problem is of practical interest for application to the on-line determination of the zinc layer thickness in the hot-dip galvanization process. In this process, a steel sheet is covered on both sides by a zinc layer following high-speed dipping of the sheet in a bath of molten zinc. The thickness of the zinc coating is measured after the process, and on-line monitoring would provide useful information for process control. Laser-ultrasonic is a noncontact remote technique well suited to this case involving hot and moving products. This problem was investigated in the present inventor's laboratory by using a set of steel specimens 0.6 mm thick, zinc coated on both sides by electro-deposition to thickness of 5, 10, and 20 μm. The sheet thickness generally ranges from 0.35 to 6 mm, 0.6 mm being a typical thickness. Electro-deposition produces specimens with uniform and fine grain layers, better suited to an initial evaluation of the technique than the less uniform and coarser grain coupons cut from hot-dip galvanized sheets. The experimental setup is the same as before, except that for laser detection a Fabry-Perot interferometer described in U.S. Pat. No. 4,659,224 Apr. 21, 1987 (Monchalin) was used. This interferometer demodulates the back-scattered light from the sample and is less sensitive to beam alignment and surface roughness. It is thus more suited for industrial applications.

The experimental results obtained with an uncoated specimen and a specimen symmetrically coated with 10 μm of zinc are shown in FIGS. 7a, 7b and 7c, 7d respectively. The thermoelastic annular source is 15 mm diameter Since the substrate cannot be considered thick (the untrasonic wavelength of the acoustic waves at 1 MHz is 3 mm in steel), the generated acoustic waves are dispersive with or without coating and an infinite number of symmetric modes ($S_0$, $S_1$, $S_2$, ...) and antisymmetric modes ($A_0$, $A_1$, $A_2$, ...) are generated. The envelopes in FIGS. 7b and 7d clearly show the results obtained by applying the TD method and reveal clearly the arrival of th $S_0$, $S_1$ and $A_0$ modes. For very small frequency*-sheet thickness products, only the first symmetric $S_0$ and antisymmetric $A_0$ modes can propagate, and the determination of their velocities can be used to estimate either the sheet thickness or elastic constants. Other modes appear above cutoff values of the frequency*-thickness products, which are multiples of $c_L/2$ and $c_T/2$ where $c_L$ and $c_T$ are respectively the longitudinal and shear velocities of the steel sheet. On sheets symmetrically coated, additional dispersion occurs due to the layered structure and the relative amplitudes of the different modes are modified.

Figure 8:
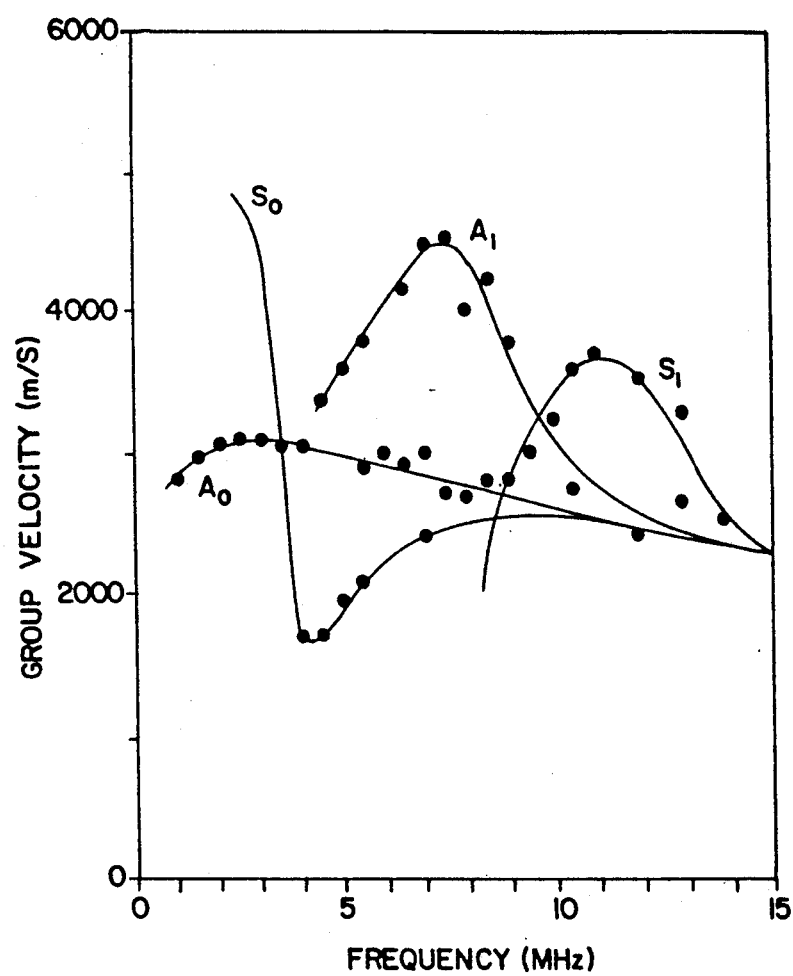
FIG. 8 is a graph showing group velocities of different modes versus frequency.
Figure 9B:
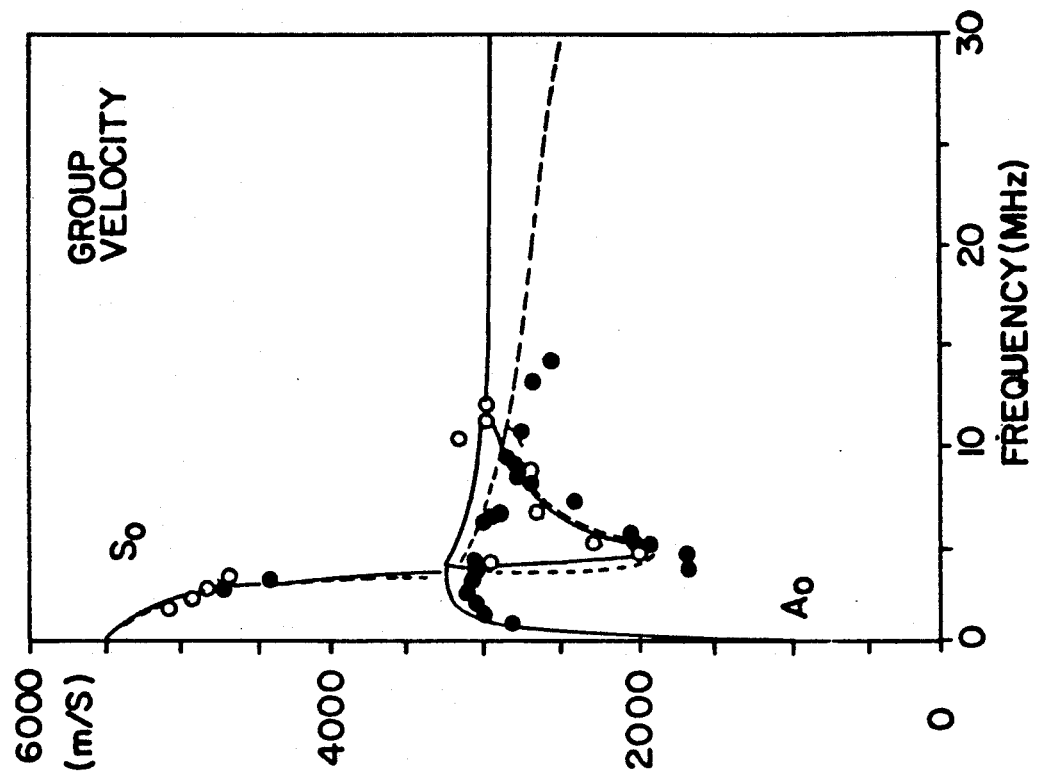
FIGS. 9a and 9b show theoretical phase and group velocities and experimental measurements.
Figure 9A:
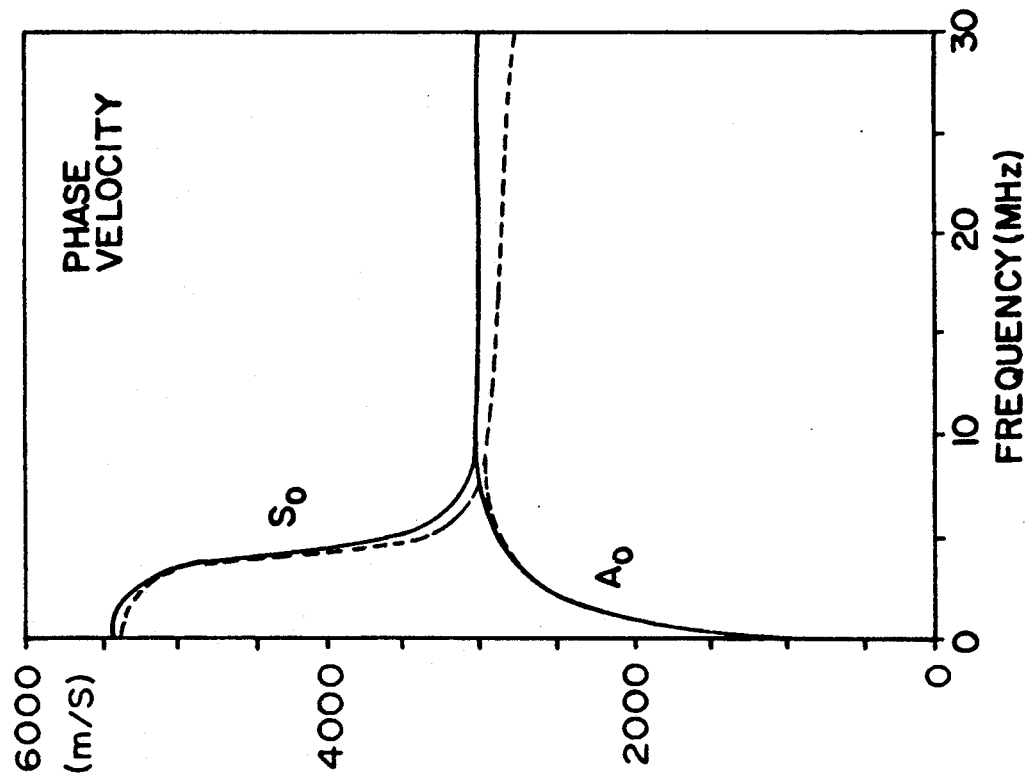
Figure 10:
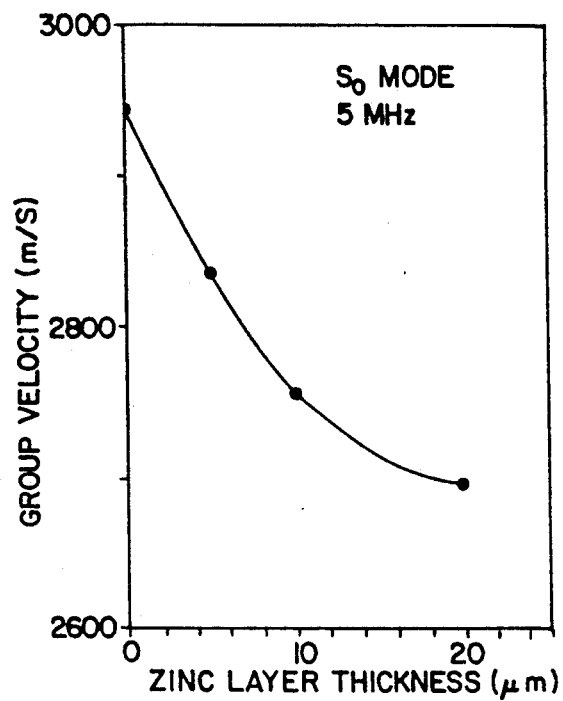
FIG. 10 shows measured group velocity of the $S_0$ mode at 12 MHz for different zinc thickness.

The TD method was used for analyzing dispersion in this case. As shown in FIGS. 7a to 7d, this method permits to show distinctly the arrival of several modes. The group velocities measured from such data versus frequency are shown for the 20 μm coated steel sheet specimens of 0.6 mm in FIG. 8. It should be noted that the spectral analysis method is not applicable in this case, since the various propagating acoustic modes cannot be separated by truncation. A comparison was also made with theory. Theoretical velocities can be calculated from the solution of the equation of motion with proper boundary conditions. FIGS. 9a and 9b show the theoretical phase and group velocities of a 0.6 mm steel sheet uncoated (solid lines) or symmetrically coated with two 20 μm zinc layers (dotted lines). Only the $A_0$ and $S_0$ modes have been plotted for sake of clarity. On the uncoated steel sheet, the velocities tend towards the steel Rayleigh velocity at high frequency, whereas on the zinc coated sheet they tend towards the zinc shear velocity. As seen in FIGS. 9a and 9b, the experimental points measured by the TD method are in good agreement with theoretical predictions. White dots are for the uncoated sheet and dark ones are for zinc coated sheet. Group velocity varies also with layer thickness for a given frequency. FIG. 10 shows for example the measured group velocity of the $S_0$ mode at 5 MHz for different zinc thickness. Such a plot can be used in principle to determine an unknown zinc thickness from the measurement of the group velocity.

Figure 11:
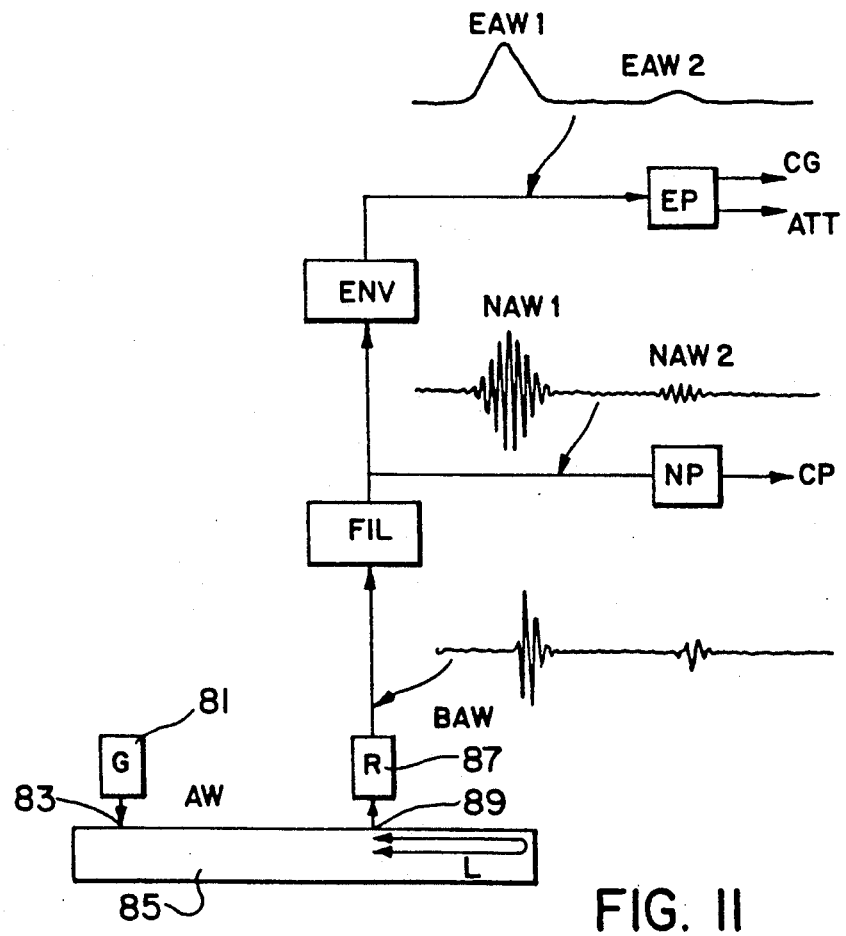
FIG. 11 is a diagrammatic illustration of the present invention according to a further embodiment.

FIG. 11 illustrates diagramatically the present invention according to still another embodiment. A frequency broadband acoustic wave (AW) is generated by a generator 81 at a location 83 in an object 85 and is detected by frequency broadband receivers 87 at only one location 89. The detected broadband wave is a combination of multiply reflected waves by the boundaries of the object. The two successive reflections corresponding to a path difference L (shown in the figure) may be separated by timing means, hence giving two broadband signals as shown by BAW in the figure. All other signal processings are same as those shown in FIG. 1.

I claim:

1. A method of measuring the characteristics of acoustic waves propagating in an object for the purpose of nondestructive evaluation of the said object, comprising steps of:
   a) generating in the said object frequency broadband acoustic waves,
   b) detecting the said acoustic waves at a first and a second locations along the said object for producing a first and a second broadband signals respectively,
   c) filtering the said first and the said second broadband signals at a center frequency F, to produce a first and a second narrow-band signals respectively, and
   d) obtaining the phase propagation time TP at the said frequency F of the said acoustic waves propagating in the said object by processing in the time-domain the said first and the said second narrow-band signals.

2. The method of measuring the characteristics of acoustic waves propagating in an object, according to claim 1, further comprising:
   e) generating a first and a second envelope signals of the said first and the second narrow-band signals respectively, each of which envelope signals indicates the energy of each of the narrow-band signals, and
   f) obtaining the group propagation time TG at the said frequency F of the said acoustic waves propagating in the said object by processing in the time-domain the said first and the second envelope signals.

3. The method of measuring the characteristics of acoustic waves propagating in an object, according to claim 2, further comprising steps of:
   g) measuring the amplitudes of the said first and second envelope signals, and
   h) obtaining the attenuation ATT at the frequency F of the said acoustic waves propagating in the said object, by using an equation $ATT = (\log R)/L$ where R is the ratio of the amplitudes of the said second and the first envelope signals and L is the distance between the said first and the second locations.

4. The method of measuring the characteristics of acoustic waves propagating in an object, according to claim 1, wherein:
   the step of detecting comprises a step of detecting the said acoustic waves at a location in the time-domain for producing the said first and the said second broadband signals when the propagating acoustic waves reflect from the boundary of the said object.

5. The method of measuring the characteristics of acoustic waves propagating in an object, according to claim 2, wherein:
   the step of detecting comprises a step of detecting the said acoustic waves at a location in the time-domain for producing the said first and the said second broadband signals when the propagating acoustic waves reflect from the boundary of the said object.

6. The method of measuring the characteristics of acoustic waves propagating in an object, according to claim 3, wherein:
   the step of detecting comprises a step of detecting the said acoustic waves at a location in the time-domain for producing the said first and the said second broadband signals when the propagating acoustic waves reflect from the boundary of the said object.

7. The method of measuring the characteristics of acoustic waves propagating in an object, according to claim 1, further comprising steps of:
   varying the said center frequency F, and
   repeating the steps (c)-(d) inclusive for each varied frequency to produce a set of phase propagation times TP in relation to frequency.

8. The method of measuring the characteristics of acoustic waves propagating in an object, according to claim 2, further comprising steps of:
   varying the said center frequency F, and
   rerepeating steps (c), (e) and (f) for each varied frequency to produce a set of group propagation times TG in relation to frequency.

9. The method of measuring the characteristics of acoustic waves propagating in an object, according to claim 3, further comprising steps of:
   varying the said center frequency F, and
   repeating steps (c), (e), (g) and (h) for each varied frequency to produce a set of attenuations ATT in relation to frequency.

10. The method of measuring the characteristics of acoustic waves propagating in an object, according to claim 7, further comprising steps of:
    processing the set of phase propagation times to detect discontinuities which may be caused by frequency dispersion and to generate a corrected set of phase propagation time TP', and
    obtaining the phase velocity CP of the acoustic waves for each varied frequency by an equation $CP = L/TP'$ where L is the distance between the said first and the said second locations.

11. The method of measuring the characteristics of acoustic waves propagating in an object, according to claim 8, further comprising a step of:

obtaining the group velocity CG of the acoustic waves for each varied frequency by an equation $$CG = L/TG$$

where L is the distance between the said first and the said second locations.

12. An apparatus for measuring the characteristics of acoustic waves propagating in an object for the purpose of nondestructive evaluation of the said object, comprising:
   a) acoustic wave generating means for generating in the said object frequency broadband acoustic waves,
   b) acoustic wave detecting means for detecting the said acoustic waves at a first and a second locations along the said object for producing a first and a second broadband signals respectively,
   c) filtering means for filtering the said first and the second broadband signals at a center frequency F to produce a first and a second narrow-band signals respectively, and
   d) narrow-band signal processing means for processing in the time-domain the first and the second narrow-band signals to determine the phase propagation time TP at the said frequency F of the acoustic waves propagating in the said object.

13. The apparatus for measuring the characteristics of acoustic waves propagating in an object, according to claim 12, further comprising:
   e) envelope generator for generating a first and a second envelope signals in response to the said first and the second narrow-band signals respectively, each of which envelope signals indicates the energy of the narrow-band signals, and
   f) envelope signal processing means for processing in the time-domain the first and the second envelope signals to determine the group propagation time TG at the said frequency F of the acoustic waves propagating in the said object.

14. The apparatus for measuring the characteristics of acoustic waves propagating in an object, according to claim 13, further comprising:
   g) amplitude means for generating amplitudes of the first and the second envelope signals, and
   h) amplitude processing means for processing the said amplitudes to obtain attenuation ATT, according to the following equation:

$$ATT = (\log R)/L$$

where R is the ratio of the amplitudes of the said second and the first envelope signals and L is the distance between the said first and the second locations.

15. The apparatus for measuring the characteristics of acoustic waves propagating in an object, according to claim 12, wherein the acoustic wave detecting means comprising:
   timing means for distinguishing the propagating acoustic waves which have reflected back from the boundary of the said object, and
   detecting means for detecting the acoustic waves in the time-domain to produce the first and the second broadband signals.

16. The apparatus for measuring the characteristics of acoustic waves propagating in an object, according to claim 13, wherein the acoustic wave detecting means comprising:
   timing means for distinguishing the propagating acoustic waves which have reflected back from the boundary of the said object, and
   detecting means for detecting the acoustic waves in the time-domain to produce the first and the second broadband signals.

17. The apparatus for measuring the characteristics of acoustic waves propagating in an object, according to claim 14, wherein the acoustic wave detecting means comprising:
   timing means for distinguishing the propagating acoustic waves which have reflected back from the boundary of the said object, and
   detecting means for detecting the acoustic waves in the time-domain to produce the first and the second broadband signals.

* * * * *